(12) United States Patent
Kim et al.

(10) Patent No.: US 11,559,699 B2
(45) Date of Patent: Jan. 24, 2023

(54) TREATMENT DEVICE USING MAGNETIC FIELD

(71) Applicant: REMED CO., LTD., Daejeon (KR)

(72) Inventors: Ghi Young Kim, Anyang-si (KR); Se Jin Yoon, Anyang-si (KR)

(73) Assignee: REMED CO., LTD., Daejeon (KR)

( * ) Notice: Subject to any disclaimer, the term of this patent is extended or adjusted under 35 U.S.C. 154(b) by 82 days.

(21) Appl. No.: 17/030,612

(22) Filed: Sep. 24, 2020

(65) Prior Publication Data
US 2022/0037071 A1 Feb. 3, 2022

(30) Foreign Application Priority Data
Jul. 31, 2020 (KR) .................. 10-2020-0095908

(51) Int. Cl.
*A61N 2/02* (2006.01)
*H01F 27/08* (2006.01)
*H01F 7/20* (2006.01)
*H05K 7/20* (2006.01)

(52) U.S. Cl.
CPC .............. *A61N 2/02* (2013.01); *H01F 7/20* (2013.01); *H01F 27/08* (2013.01); *H05K 7/20145* (2013.01)

(58) Field of Classification Search
CPC ........... A61N 2/02; H01F 27/08; H01F 27/10; H01F 27/105; H01F 27/16; H01F 27/025; H05K 7/20145
See application file for complete search history.

(56) References Cited

U.S. PATENT DOCUMENTS

| 6,527,694 | B1 | 3/2003 | Ishikawa et al. | |
|---|---|---|---|---|
| 2001/0012912 | A1 | 8/2001 | Feucht | |
| 2006/0004244 | A1* | 1/2006 | Phillips | A61N 2/006 600/13 |
| 2009/0108969 | A1 | 4/2009 | Sims et al. | |
| 2011/0021863 | A1 | 1/2011 | Burnett et al. | |
| 2016/0030763 | A1 | 2/2016 | Midorikawa et al. | |

FOREIGN PATENT DOCUMENTS

| CN | 203123344 | 8/2013 |
|---|---|---|
| CN | 105050658 | 11/2015 |
| EP | 3340420 | 6/2018 |
| JP | 5196322 | 5/2013 |
| KR | 10-0575541 | 5/2006 |
| KR | 20-2020-0000889 | 5/2020 |
| WO | 2017-212253 | 12/2017 |

\* cited by examiner

*Primary Examiner* — Carrie R Dorna
(74) *Attorney, Agent, or Firm* — Lex IP Meister, PLLC

(57) ABSTRACT

The present invention relates to a treatment device using a magnetic field, which includes a coil generating a pulse magnetic field and a cooling unit.

The treatment device using a magnetic field in accordance with an embodiment of the present invention includes: a magnetic field generating coil disposed below a contact surface that closely contacts a portion of a body; a cooling unit configured to supply a fluid that cools the magnetic field generating coil; and a duct configured to guide the fluid between the cooling unit and the magnetic field generating coil. Here, the cooling unit is disposed below the magnetic field generating coil and disposed so that an angle between a fluid supply direction from the cooling unit and a central axis of the magnetic field generating coil is equal to or less than the right angle.

8 Claims, 4 Drawing Sheets

[FIG. 1]
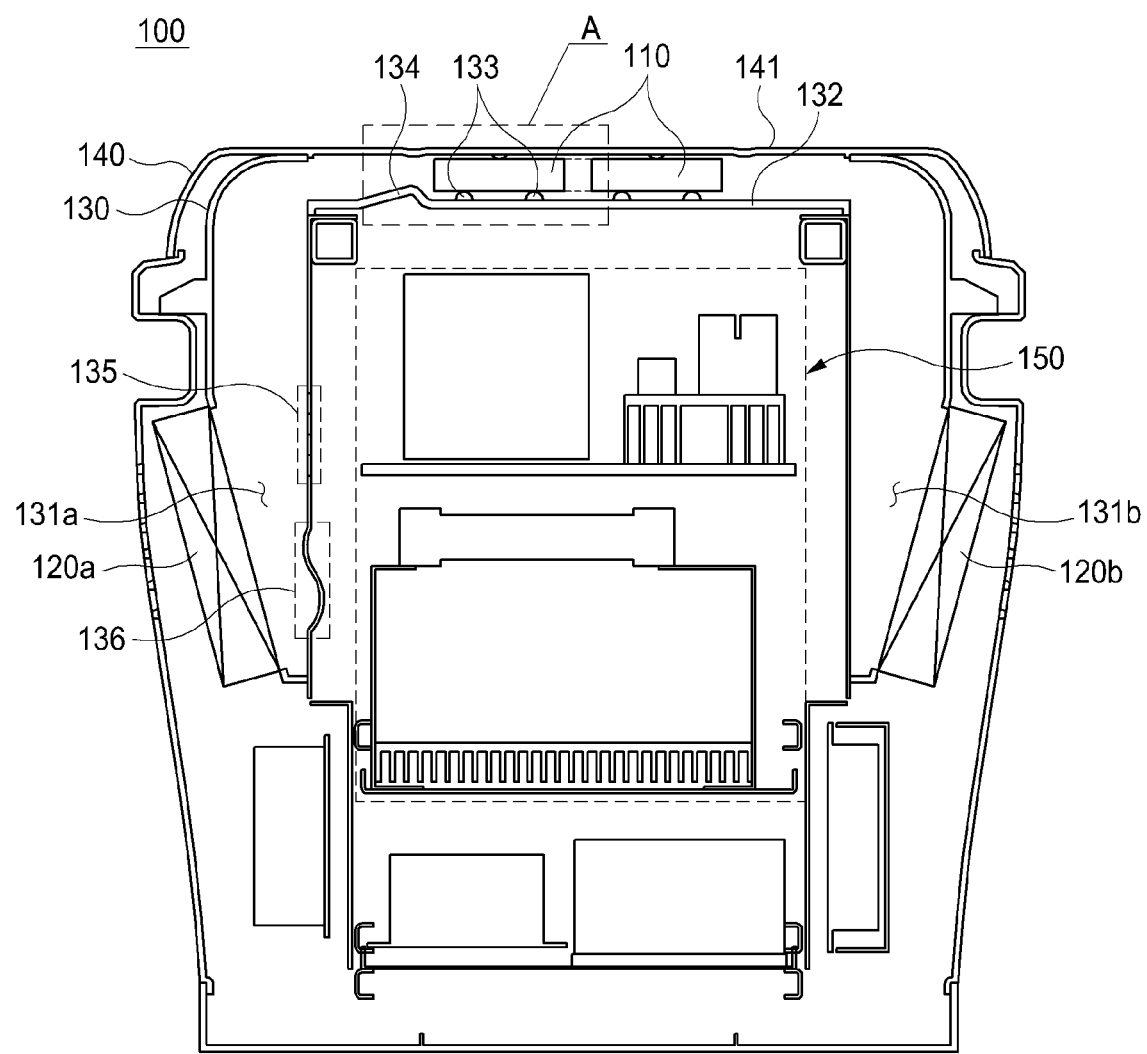

[FIG. 2]
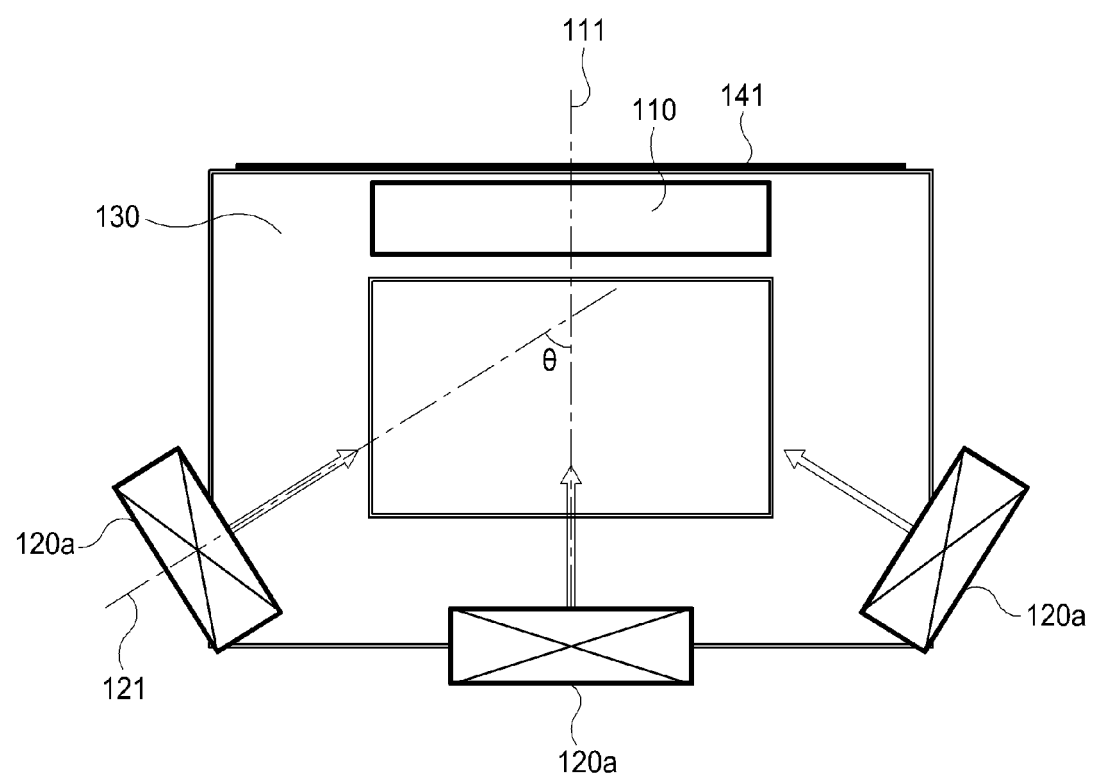

[FIG. 3]
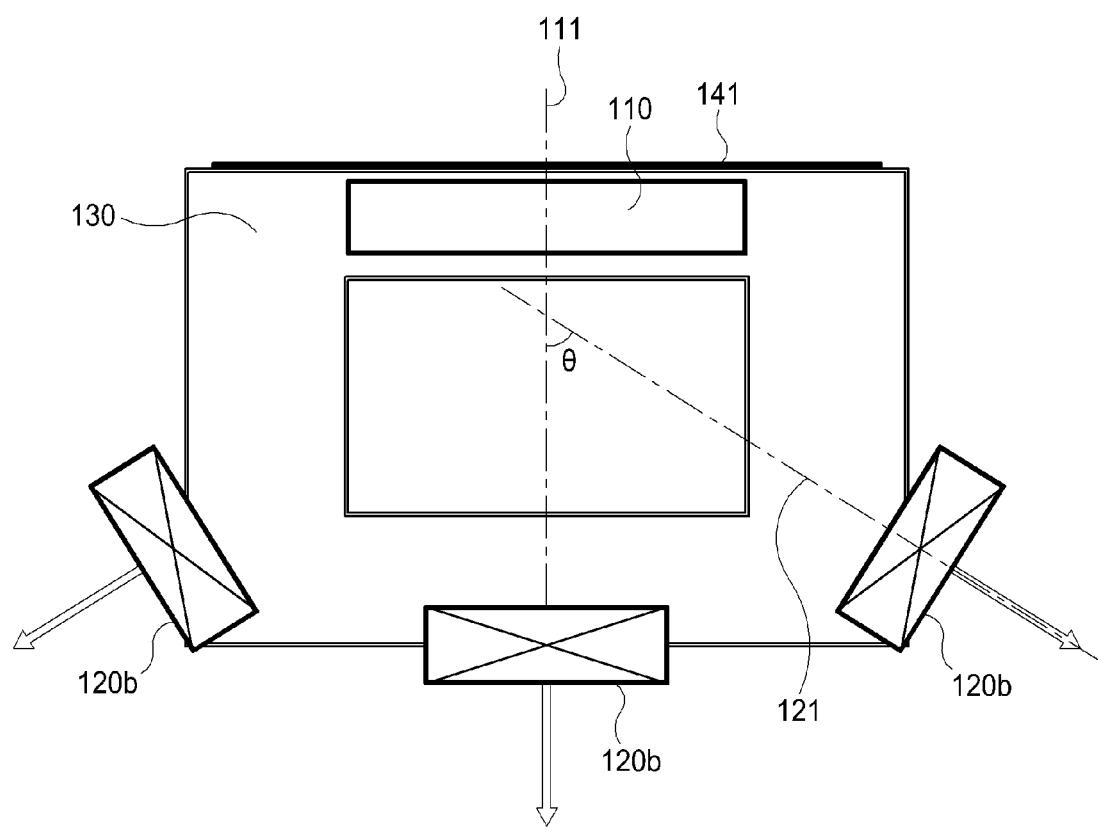

【FIG. 4】
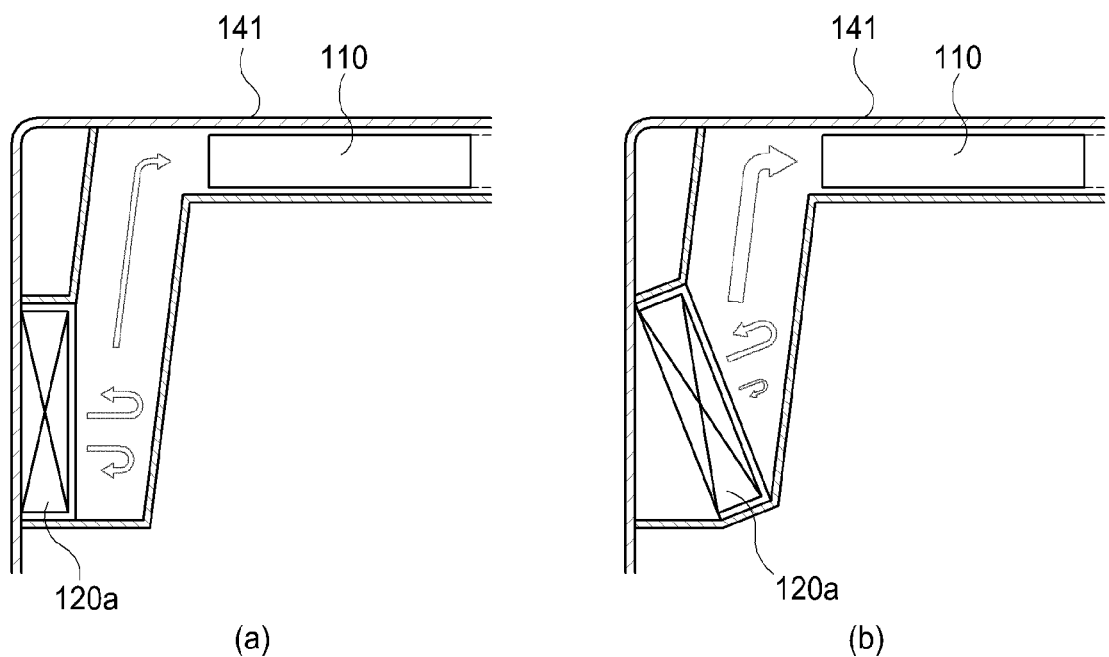
【FIG. 5】
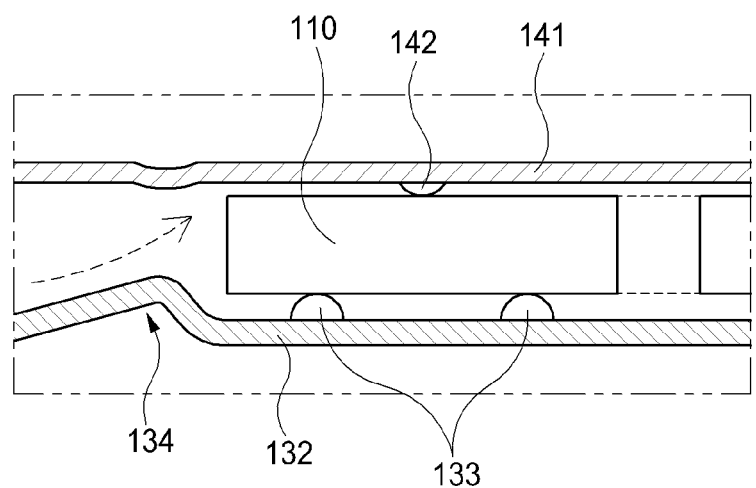

TREATMENT DEVICE USING MAGNETIC FIELD

CROSS-REFERENCE TO RELATED APPLICATIONS

This U.S. non-provisional patent application claims priority under 35 U.S.C. § 119 of Korean Patent Application No. 10-2020-0095908, filed on Jul. 31, 2020, the entire contents of which are hereby incorporated by reference.

TECHNICAL FIELD

The present invention disclosed herein relates to a treatment device using a magnetic field, and more particularly, to a treatment device using a magnetic field, which includes a coil generating a pulse magnetic field and a cooling unit.

BACKGROUND ART

In general, a treatment device using a magnetic field induces a magnetic field by applying a pulse-type current and stimulates an affected area by inducing a current caused by the generated magnetic field into a human tissue. The treatment device using a magnetic field includes a coil generating a magnetic field by using a current applied from a main body and generates a magnetic field having a desired intensity by applying a current of several thousands amperes for a short time (50 μs to 300 μs).

Heat is inevitably generated when a current flows through the coil, and the heat increases an internal resistance of the coil and an inductance of the coil. Thus, a typical treatment device using a magnetic field essentially includes a cooling unit capable of cooling the coil.

The cooling unit uses various methods including a water-cooling method using water, an air-cooling method that discharges heat by using a heat dissipation plate, etc., and then cools the discharged heat through a fan, etc., and an oil-cooling method that allows an oil to pass around the coil and then cools the heat absorbed oil.

The typically used water-cooling method is easily maintained and has a cooling efficiency greater than that of each of the air-cooling method and the oil-cooling method. However, the water-cooling method has a limitation of a low cooling efficiency because cooling water may not directly contact the coil through which a high-voltage current flows but indirectly flows around the coil to cool the coil. Also, the water-cooling method has a limitation in that since a risk of leakage and external case damage exists, a complete insulation process is required.

On the other hand, the typically used air-cooling method has a limitation of a lower cooling efficiency, and the oil-cooling method has a limitation of a low cooling efficiency because a high risk of leakage exists, and an oil has a property of slowly heated and slowly cooled. Also, although some treatment devices adopt a compressor or radiator method as the cooling unit, the compressor or radiator method has a great limitation of vibrations and noises and may not exactly control a temperature.

DISCLOSURE OF THE INVENTION

Technical Problem

The present invention provides a treatment device using a magnetic field, which include a cooling unit capable of effectively cooling heat generated from a magnetic field generating coil.

The present invention also provides a treatment device using a magnetic field, which is a chair-type treatment device having a compact structure and a high cooling efficiency by designing an effective duct structure.

The present invention also provides a treatment device using a magnetic field, which is capable of enhancing convenience of a user by adopting a structure capable of reducing vibrations and noises during operation.

Technical Solution

In accordance with an embodiment of the present invention, a treatment device using a magnetic field includes: a magnetic field generating coil disposed below a contact surface that closely contacts a portion of a body; a cooling unit configured to supply a fluid that cools the magnetic field generating coil; and a duct configured to guide the fluid between the cooling unit and the magnetic field generating coil. Here, the cooling unit is disposed below the magnetic field generating coil and disposed so that an angle between a fluid supply direction from the cooling unit and a central axis of the magnetic field generating coil is equal to or less than the right angle.

In an embodiment, the cooling unit may include an inlet cooling unit configured to supply a fluid to the magnetic field generating coil and an outlet cooling unit configured to exhaust a fluid passed through the magnetic field generating coil to the outside.

In an embodiment, the inlet cooling unit and the outlet cooling unit may be disposed symmetrically with respect to the magnetic field generating coil.

In an embodiment, the duct may have one end opened to the inlet cooling unit and the other end opened to the outlet cooling unit and guide a fluid introduced from the inlet cooling unit to pass through the magnetic field generating coil and be exhausted through the outlet cooling unit.

In an embodiment, the duct may include: a seated surface on which the magnetic field generating coil is seated at a position corresponding to the contact surface; and a support disposed on the seated surface to support the magnetic field generating coil.

In an embodiment, the duct may be formed such that an internal cross-section of an area in which the magnetic field generating coil is disposed is less than a cross-section of each of the one end and the other end.

In an embodiment, the duct may include a protruding portion that protrudes to the magnetic field generating coil from the seated surface in at least a partial area of the seated surface formed between the inlet cooling unit and the magnetic field generating coil.

In an embodiment, the duct may include a hole configured to allow a portion of the introduced fluid to pass therethrough in at least a partial area between the inlet cooling unit and the magnetic field generating coil.

In an embodiment, at least a portion of an inner circumferential surface of the duct between the inlet cooling unit and the magnetic field generating coil may have a curved shape.

In an embodiment, the contact surface may include a support that protrudes to the magnetic field generating coil from a bottom surface thereof.

Advantageous Effects

The treatment device using a magnetic field of the present invention may effectively cool the heat generated from the magnetic field generating coil. Particularly, the cooling efficiency at the contact surface that closely contacts the body of the user may improve.

Also, the treatment device using a magnetic field of the present invention may provide a chair-type treatment device having a compact structure and simultaneously increasing the cooling efficiency by designing an effective duct structure.

Also, the treatment device using a magnetic field of the present invention may reduce the vibration and the noise generated during operation.

BRIEF DESCRIPTION OF THE DRAWINGS

FIG. 1 is a cross-sectional view illustrating a treatment device using a magnetic field of the present invention.

FIG. 2 is a schematic conceptual view illustrating a disposed position of an inlet cooling unit in accordance with the present invention.

FIG. 3 is a schematic conceptual view illustrating a disposed position of an outlet cooling unit in accordance with the present invention.

FIG. 4 is a cross-sectional view for comparing and explaining a cooling structure of present invention.

FIG. 5 is an enlarged cross-sectional view illustrating region A of FIG. 1.

MODE FOR CARRYING OUT THE INVENTION

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present disclosure to those skilled in the art. Further, the present disclosure is only defined by scopes of claims.

It will be understood that although the terms of first and second are used herein to describe various elements, these elements should not be limited by these terms. These terms are only used to distinguish one component from another component. Accordingly, a first component that will be described below may be a second component within the technical idea of the present disclosure.

The meaning of "include," "comprise," "including," or "comprising," specifies a property, a region, a fixed number, a step, a process, an element and/or a component but does not exclude other properties, regions, fixed numbers, steps, processes, elements and/or components.

Also, for convenience of description, the dimensions of elements are exaggerated or downscaled. Therefore, it will be understood that the embodiments disclosed in this specification includes some variations without limitations to the shapes as illustrated in the figures.

Like reference numerals refer to like elements throughout.

It will also be understood that when an element is referred to as being "'connected to" or "engaged with" another element, it can be directly connected to the other element, or intervening elements may also be present. It will also be understood that when an element is referred to as being 'directly connected to' another element, there is no intervening elements.

It will also be understood that when a layer is referred to as being "on" another layer or substrate, it can be directly on the other layer or substrate, or intervening layers may also be present. In contrast, when an element is referred to as being "directly on" another element or layer, there are no intervening elements or layers present.

Spatially relative terms, such as "below", "beneath", "lower", "above", "upper" and the like, may be used herein for ease of description to describe one element or feature's relationship to another element(s) or feature(s) as illustrated in the figures. The spatially relative terms should be understood as terms which include different directions of configurative elements in addition to directions illustrated in the figures when using or operating the inventive concept.

Features of various embodiments of the present disclosure are partially or entirely coupled or combined with each other, and technically various interlocking and driving are enabled. Also, the embodiments may be independently performed with respect to each other, or performed in combination of each other.

Hereinafter, a treatment device using a magnetic field of the present invention will be described in detail with reference to the accompanying drawings.

FIG. 1 is a cross-sectional view illustrating a treatment device using a magnetic field of the present invention, FIG. 2 is a schematic conceptual view illustrating a position of an inlet cooling unit in accordance with the present invention, FIG. 3 is a schematic conceptual view illustrating a position of an outlet cooling unit in accordance with the present invention, FIG. 4 is a cross-sectional view for comparing and explaining a cooling structure of the present invention, and FIG. 5 is an enlarged cross-sectional view illustrating region A of FIG. 1.

Referring to FIG. 1, a treatment device 100 using a magnetic field (hereinafter, referred to as a magnetic field generating treatment device 100) of the present invention includes a magnetic field generating coil 110, a cooling unit 120, a fluid guide duct 130, a housing 140, and an internal electronic device 150. Here, since the above-described components are not essential for implementing the magnetic field generating treatment device 100, the magnetic field generating treatment device 100 may include more or less components than the above-described components. Also, each of the components may be constituted as a separate chip, module, or device, or be contained in one device.

The magnetic field generating coil 110 generates a pulse magnetic field through an applied current. The magnetic field generating coil 110 is disposed below a contact surface 141 that closely contacts a portion of a body.

The cooling unit 120 supplies a fluid for cooling the magnetic field generating coil 110.

Referring to FIG. 1, the cooling unit 120 includes an inlet cooling unit 120a supplying a fluid to the magnetic field generating coil 110 and an outlet cooling unit 120b exhausting the fluid passed through the magnetic field generating coil 110 to the outside.

The inlet cooling unit 120a and the outlet cooling unit 120b may be disposed symmetrically with respect to magnetic field generating coil 110.

The inlet cooling unit 120a supplies a fluid from the outside to the inside of the magnetic field generating treatment device 100 of the present invention. Here, the inlet cooling unit 120a may be one selected from a fan, a blower, a compressor, and a pump. Referring to FIG. 2, the inlet cooling unit 120a is disposed below the magnetic field generating coil 110. The inlet cooling unit 120a is disposed so that an angle θ between a fluid supply direction 121 from the inlet cooling unit 120a and a central axis 111 of the magnetic field generating coil 110 is equal to or less than the right angle.

The outlet cooling unit 120b exhausts a fluid flowing in the magnetic field generating treatment device 100 to the outside. Here, the outlet cooling unit 120b may be one selected from a fan, a blower, a compressor, and a pump. Referring to FIG. 3, the outlet cooling unit 120b is disposed below the magnetic field generating coil 110. The outlet cooling unit 120b is disposed so that an angle θ between a fluid supply direction 121 from the outlet cooling unit 120b and a central axis 111 of the magnetic field generating coil 110 is equal to or less than the right angle.

Here, the angle θ between the fluid supply direction 121 and the central axis 111 of the magnetic field generating coil 110 may be greater than 0° and less than 90°, preferably greater than 10° and equal to or less than 60°.

Advantages of forming a predetermined angle between the fluid supply direction 121 from the inlet cooling unit 120a and the central axis 111 of the magnetic field generating coil 110 will be described with reference to FIGS. 4A and 4B.

As the angle θ between the fluid supply direction 121 from each of the inlet cooling unit 120a and the outlet cooling unit 120b and the central axis 111 of the magnetic field generating coil 110 is set to a preset angle, the magnetic field generating treatment device 100 may improve the cooling efficiency of the magnetic field generating coil 110 instead of arranging the cooling unit 120 on the same plane as the magnetic field generating coil 110.

FIG. 4A is a view illustrating a case when the angle between the fluid supply direction 121 from the inlet cooling unit 120a and the central axis 111 of the magnetic field generating coil 110 is 90°. In this case, the fluid supplied from the inlet cooling unit 120a is not supplied to the magnetic field generating coil 110 but return to the inlet cooling unit 120a by an inner circumferential surface of the duct 130. Since this arrangement does not effectively move the fluid supplied from the inlet cooling unit 120a to the magnetic field generating coil 110, the cooling efficiency of the magnetic field generating treatment device 100 may be degraded. However, FIG. 4B is a view illustrating a case when the fluid supply direction 121 from the inlet cooling unit 120a forms a predetermined angle with the central axis 111 of the magnetic field generating coil 110. In this case, the fluid supplied from the inlet cooling unit 120a heads toward the magnetic field generating coil 110, the magnetic field generating treatment device 100 has an advantage in that the fluid supplied from the inlet cooling unit 120a may be effectively moved to the magnetic field generating coil 110.

Furthermore, as the angle θ between the fluid supply direction 121 from each of the inlet cooling unit 120a and the outlet cooling unit 120b and the central axis 111 of the magnetic field generating coil 110 is set to the preset angle, an overall volume of the magnetic field generating treatment device 100 of the present invention may be reduced. As illustrated in FIG. 1, as a groove is defined in an area of the housing 140 between the cooling unit 120 and the magnetic field generating coil 110, a user may use the groove as a handle to thus improve usage convenience. Also, as the angle θ between the fluid supply direction 121 from each of the inlet cooling unit 120a and the outlet cooling unit 120b and the central axis 111 of the magnetic field generating coil 110 is set to the preset angle, a limitation of introducing dusts existing at a bottom portion into the device may be prevented although the inlet cooling unit 120a adopts one of a fan, a blower, a compressor, and a pump.

Referring to FIG. 1, the duct 130 guides the fluid between the cooling unit 120 and the magnetic field generating coil 110.

Specifically, the duct 130 has one end 131a opened to the inlet cooling unit 120a and the other end 131b opened to the outlet cooling unit 120b. The duct 130 guides the fluid introduced from the inlet cooling unit 120a to pass through the magnetic field generating coil 110 and be discharged through the outlet cooling unit 120b.

The duct 130 is formed such that an internal cross-section of an area in which the magnetic field generating coil 110 is disposed is less than a cross-section of each of the one end 131a and the other end 131b. In other words, the duct 130 is formed such that a cross-section of an area in which a seated surface 132 is provided is less than that of each of the one end 131a and the other end 131b. Since a velocity of the fluid increases in an area in which the internal cross-section decreases, the duct 130 has a structure in which the velocity of the fluid increases in the area in which the magnetic field generating coil 110 is disposed.

The duct 130 includes the seated surface 132 on which the magnetic field generating coil 110 is seated at a position corresponding to the contact surface 141.

The magnetic field generating coil 110 is seated on the seated surface 132, and the duct 130 includes support 133 supporting the magnetic field generating coil 110 at a position corresponding to the seated position. The support 133 allows the magnetic field generating coil 110 to be spaced a predetermined distance from the inner circumferential surface of the duct 130. The fluid supplied from the inlet cooling unit 120a flows through the space spaced by the support 133.

The support 133 may be rubber. The support 133 may serve to absorb a vibration generated when the magnetic field generating coil 110 operates.

Referring to FIGS. 1 and 5, the duct 130 includes a protruding portion 134 protruding from the seated surface 132 toward the magnetic field generating coil 110. The protruding portion 134 is provided in at least a portion of the seated surface 132 provided between the inlet cooling unit 120a and the magnetic field generating coil 110.

As illustrated in FIG. 5, the protruding portion 134 guides the fluid introduced from the inlet cooling unit 120a to flow toward an upper portion of the magnetic field generating coil 110. In other wards, the protruding portion 134 guides the fluid introduced from the inlet cooling unit 120a to flow toward an area between the magnetic field generating coil 110 and the contact surface 141. The protruding portion 134 may improve the cooling efficiency of the portion closely contacting a portion of the body of the user by increasing a flow velocity and a flow rate supplied to the area between the magnetic field generating coil 110 and the contact surface 141.

Although the protruding portion 134 is formed by bending a portion of the inner circumferential surface of the duct 130 in the present invention, the embodiment of the present invention is not limited thereto. For example, the protruding portion 134 may be formed in various methods such as a method of attaching a separate member to a portion of the inner circumferential surface of the duct 130.

Referring to FIG. 1, the duct 130 includes a hole 135 defined in at least a portion of an area between the inlet cooling unit 120a and the magnetic field generating coil 110.

The hole 135 allows a portion of the fluid introduced to the duct 130 to pass therethrough. The fluid passed through the hole 135 may cool the internal electronic device 150. As the duct 130 includes the hole 135, a portion of the fluid introduced from the inlet cooling unit 120a may be used to cool heat generated from the magnetic field generating coil 110, and the rest thereof may be used to cool heat generated from the internal electronic device 150. Here, the number and size of the hole 135 may be determined so that about 70% of the fluid supplied to the hole 135 flows to the magnetic field generating coil 110, and about 30% thereof flows to the internal electronic device 150.

The duct 130 may simultaneously cool the magnetic field generating coil 110 and the internal electronic device 150 by including the hole 135. Through this, the magnetic field generating treatment device 100 of the present invention may increase the cooling efficiency through a compact structure thereof instead of including a separate cooling unit for the internal electronic device 150.

Referring to FIG. 1, the duct 130 may include a curved portion 136 obtained by bending at least a portion of the inner circumferential surface between the inlet cooling unit 120a and the magnetic field generating coil 110.

Although the curved portion 136 is formed by bending a portion of the inner circumferential surface of the duct 130 in the present invention, the embodiment of the present invention is not limited thereto. For example, the curved portion 136 may have an embossing shape or be formed in various methods such as a method of attaching a separate member to a portion of the inner circumferential surface of the duct 130.

The duct 130 may reduce a noise generated when a fan or a blower is used by including the curved portion 136. A noise generated when the fluid introduced from the inlet cooling unit 120a contacts the curved portion 136 of the duct 130 may be less than that generated when the fluid introduced from the inlet cooling unit 120a contacts other areas of the duct 130.

Referring to FIG. 1, the contact surface 141 includes a support 142 protruding from a bottom surface of the contact surface 141 to the magnetic field generating coil 110. Here, the contact surface 141 may be a portion of the housing 140 or a portion of the duct 130.

The support 142 allows the magnetic field generating coil 110 to be spaced a predetermined distance from the contact surface 141. The fluid supplied from the inlet cooling unit 120a flows through the space spaced by the support 142. The support 142 may be rubber like the support 133 provided on the seated surface 132. The support 142 may serve to absorb a vibration generated when the magnetic field generating coil 110 operates.

The magnetic field generating treatment device of the present invention may effectively cool the heat generated from the magnetic field generating coil. Particularly, the cooling efficiency at the contact surface that closely contacts the body of the user may improve. Also, the magnetic field generating treatment device of the present invention may provide a chair-type treatment device having a compact structure and simultaneously increasing the cooling efficiency by designing an effective duct structure. Also, the magnetic field generating treatment device of the present invention may reduce the vibration and the noise generated during operation.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A treatment device using a magnetic field, comprising:
   a magnetic field generating coil disposed below a contact surface that is configured to closely contact a portion of a body;
   a cooling unit configured to supply a fluid that cools the magnetic field generating coil; and
   a duct forming a rigid flow path of the fluid between the cooling unit and the magnetic field generating coil,
   wherein the fluid is air flowing along the duct,
   wherein the cooling unit is disposed at an open end of the duct to supply the air into the duct, disposed below the magnetic field generating coil and disposed so that an angle between a fluid supply direction from the cooling unit and a central axis of the magnetic field generating coil is equal to or less than 90°,
   wherein the duct comprises a seated surface on which the magnetic generating coil is seated, and the seated surface is disposed to face the contact surface,
   wherein the cooling unit comprises an inlet cooling unit configured to supply the fluid to the magnetic field generating coil and an outlet cooling unit configured to exhaust the fluid passed through the magnetic field generating coil to an outside,
   wherein the duct has one end opened to the inlet cooling unit and another end opened to the outlet cooling unit and guides the fluid introduced from the inlet cooling unit to pass through the magnetic field generating coil and be exhausted through the outlet cooling unit.

2. The treatment device of claim 1, wherein the inlet cooling unit and the outlet cooling unit are disposed symmetrically with respect to the magnetic field generating coil.

3. The treatment device of claim 1, wherein the duct comprises: a support disposed on the seated surface to support the magnetic field generating coil.

4. The treatment device of claim 3, wherein the duct comprises a protruding portion that protrudes to the magnetic field generating coil from the seated surface in at least a partial area of the seated surface formed between the inlet cooling unit and the magnetic field generating coil.

5. The treatment device of claim 1, wherein the duct is formed such that an internal cross-section of an area in which the magnetic field generating coil is disposed is less than a cross-section of each of the one end and the other end.

6. The treatment device of claim 1, wherein the duct comprises a hole configured to allow a portion of the fluid to pass therethrough in at least a partial area between the inlet cooling unit and the magnetic field generating coil.

7. The treatment device of claim 1, wherein at least a portion of an inner circumferential surface of the duct between the inlet cooling unit and the magnetic field generating coil has a curved shape.

8. The treatment device of claim 1, wherein the contact surface comprises a support that protrudes to the magnetic field generating coil from a bottom surface thereof.

* * * * *